(12) United States Patent
Mullen et al.

(10) Patent No.: US 7,689,274 B2
(45) Date of Patent: Mar. 30, 2010

(54) BRAIN-WAVE AWARE SLEEP MANAGEMENT

(75) Inventors: Tim R. Mullen, San Pablo, CA (US); Qingfeng Huang, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 188 days.

(21) Appl. No.: 11/947,930

(22) Filed: Nov. 30, 2007

(65) Prior Publication Data

US 2009/0143636 A1    Jun. 4, 2009

(51) Int. Cl.
*A61B 5/00* (2006.01)
(52) U.S. Cl. ...................................... 600/544; 600/545
(58) Field of Classification Search ........................ None
See application file for complete search history.

(56) References Cited

U.S. PATENT DOCUMENTS 6,625,485 B2*  9/2003  Levendowski et al. ...... 600/544
2006/0293608 A1* 12/2006 Rothman et al. ............ 600/545

* cited by examiner

*Primary Examiner*—Robert L Nasser
(74) *Attorney, Agent, or Firm*—Marger Johnson & McCollom, P.C.

(57) ABSTRACT

A system includes a port to receive brain activity data of a user, a processor to detect a beginning time of a user nap based upon the brain activity data, and a user interface to notify the user when a predetermined nap time has elapsed. A method of monitoring a user somnolence level receives brain activity data from a user, and determines a somnolence level from the brain activity data. If the somnolence level is sleep, the system determines if a nap has progressed to a waking point, and if the nap has progressed to a waking point, alerts the user.

17 Claims, 4 Drawing Sheets

BRAIN-WAVE AWARE SLEEP MANAGEMENT

BACKGROUND

A large body of research shows that occasional catnaps lead to increased productivity in the work place. Managing one's time around naps, as well as optimizing the timing and length of naps, presents challenges and may cause reluctance to take naps. One user may hesitate to doze off while reading a lengthy document for fear of over sleeping. Another user may be in the middle of a time 'crunch' and need to stay awake while reading the same document.

In more everyday situations, people generally have regular patterns of drowsiness over the course of a day, such as being sleepy after lunch, or in the later afternoon. Visualizing and incorporating this information into a schedule also presents several challenges. Many users would probably find it useful to have information about their fatigue/drowsiness patterns during the day. They could use it to arrange their schedules, for example.

DETAILED DESCRIPTION OF THE EMBODIMENTS

Figure 1:
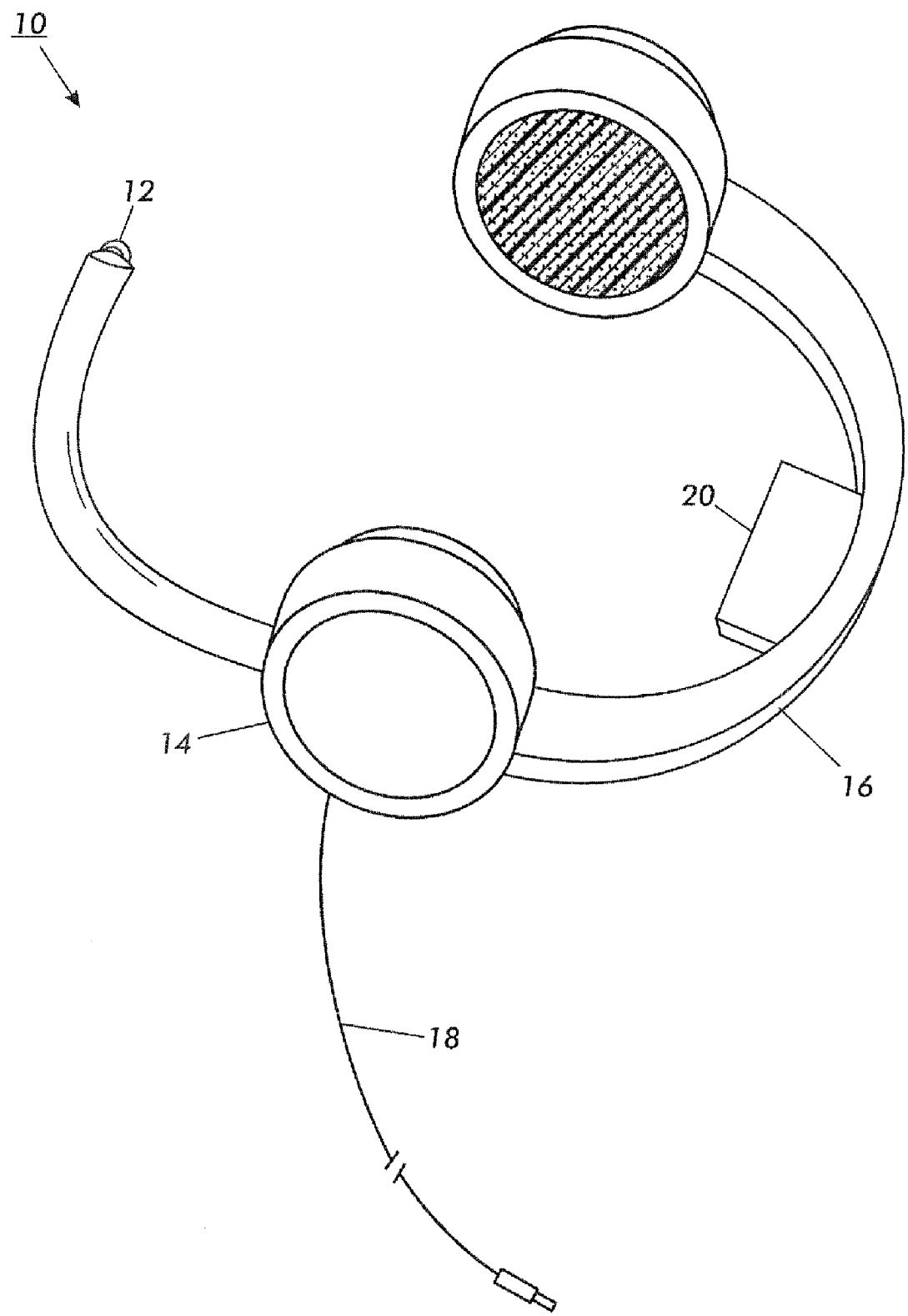
FIG. 1 shows an example of an electroencephalogram headset.

FIG. 1 shows an example of an electroencephalogram (EEG) headset. It must be noted that this is just one example and several other types of headsets or electrode holders may also fall within the scope of the invention as claimed. For example, this headset includes an earphone component that may allow a user to listen to music, but some applications would render earphones undesirable.

The headset 10 comprises an electrode 12 attached to one of the ear cups 14 of a pair of earphones 16. Generally, electrodes used in EEGs require a gel between the electrode and the skin. However, recent developments in electrode technologies have resulted in 'dry' electrodes that do not require the gel. Daily use by most users would seem to require 'gel-less' electrodes, or the users will not use the headsets. One example is the dry electrode technology available from Neurosky™ in their ThinkGear™ module.

The headset 10 includes a wire 18 that connects the headset to another device, such as a laptop computer, not shown. The connection would allow transmission of signals both to and from the user. For example, the user may listen to music playing on the laptop, such as from a compact disc (CD) or MP3 music files. At the same time, signals from the electrode will transmit to the laptop for either real-time or later analysis. An alternative configuration of headset could be a headband type configuration with the electrodes inside a comfortable headband.

With the improvements in miniaturization and power management, the possibility exists that the headset could become wireless. The user could send and receive signals using wireless technology, such as Bluetooth® technology, similar to cell phone wireless headsets, etc. In the embodiment of FIG. 1, the headset receives power from a battery pack 20. However, using a technology such as USB 2.0, where the device receives power from a USB port on a computer, the battery may become redundant. Alternatively, the battery could also power the wireless transmitter.

In the example above, a laptop or other local computing device received the signals for analysis. This consists of merely one example, as with improvements in wireless technology and miniaturization, the signals could be transmitted to a more remote computer, or even through a wireless access point to a central store. In the example where a local computer receives the signals, the signals could in turn travel to a central store, or other repository for analysis, storage or both. Another possibility involves a processor resident in the headset to also do the analysis. In current circumstances, with current processors, power sources and computing speeds, the analysis will more than likely occur at the local computing device.

The analysis may include many different tasks. For example, the design must select which types of activity to analyze. Much of this will depend upon the nature of the inputs. In the example above, where only one electrode exists, certain representations of the raw data work better than others. For other systems, that may use two or more electrodes, other types of representations may have better accuracy.

The design would then differentiate features of the data, depending upon the nature of the application that will use the data. A 'feature' of the data consists of some characteristic, such as a peaks, clusters, phase coherence, etc., that the data analysis will use to determine the meaning of the data.

Once the system has identified the significant features, it then classifies the features. In this particular example, the classification will include a user's mental state, such as boredom, confusion, frustration, interest, etc. One aspect of the mental state could be interest levels in content as the content is presented. Applications can the use the mental state data for various purposes, including as a feedback signal or mechanism.

Figure 2:
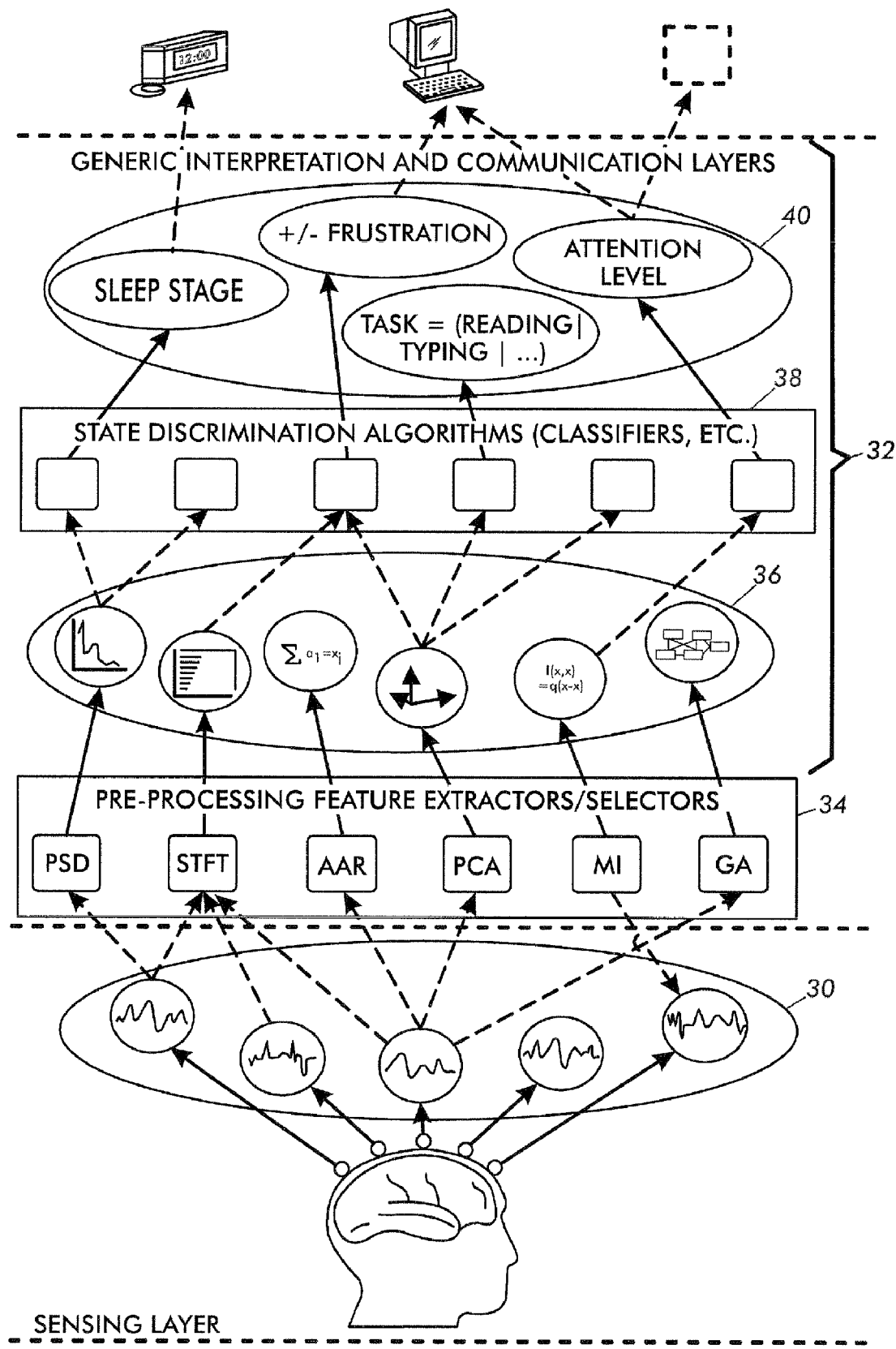
FIG. 2 shows an embodiment of an architecture for analyzing brain waves in computing.

FIG. 2 shows an architecture of a system that selects and classifies the features of brain wave data and then provides it to various applications. The sensing layer 30 may produce a 'tuplespace' or associative memory structure. The memory structure consists of tuples, or ordered and time stamped collections of values such as <Electrode 1, [data stream]>. The tuples are then provided to the generic interpretation and communications layer 32.

Within the layer 32, the rectangles such as 34 represent process layers and the ovals such as 36 represent data spaces. The processes, such as 38 can operate asynchronously on the data in the adjacent data spaces. This modularizes the different levels of processing referred to above. Developers working within one layer need not have in-depth expertise regarding implementations of other layers or processes, even within the same layer. Examples of feature extracting methods in 34 may include Principle Component Analysis (PCA), genetic algorithms (GA), Short Time Fourier Transformation (STFT), Adaptive Autoregressive method (AAR), and Power Spectrum Density (PSD).

The 'top' of the communication at data space 40 then provides the resulting data to applications that use the data for their own purposes. In this example, the application uses the data to provide feedback to the user as to the level of the user's brain activity. In this system, the application would be a 'catnapper' application that allows users to track and monitor their drowsiness levels to optimize their napping behavior.

Figure 3:
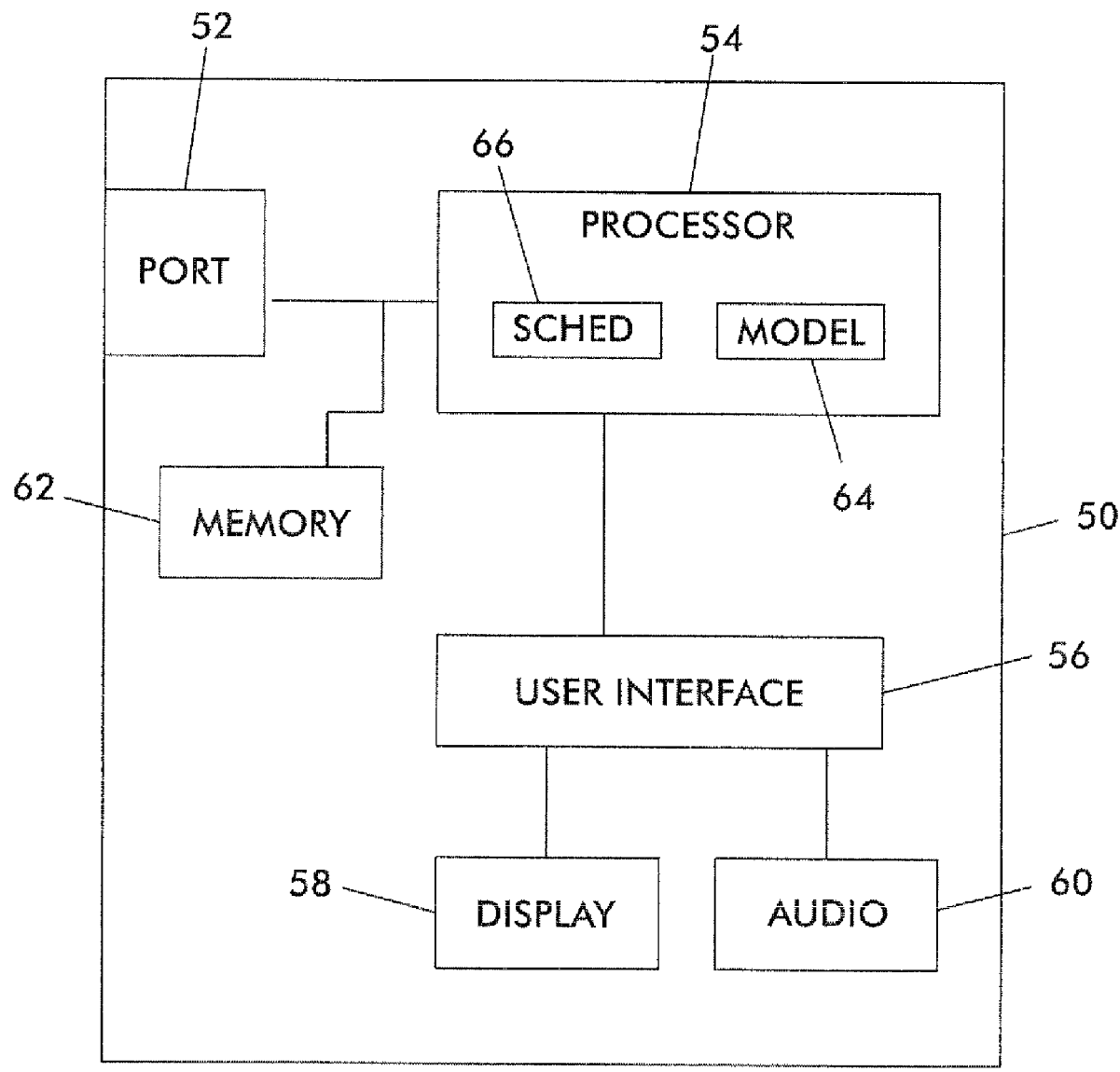
FIG. 3 shows an embodiment of catnapping monitoring system.

FIG. 3 shows an example of a catnapper system that allows a user to track and monitor their drowsiness. The system may consist of any electronics device that can receive signals from the electrode, either through a wired or wireless connection, process them to determine user brain activity and somnolence level, and provide some sort of feedback to the user. Examples include laptop computers, cell phones or personal digital assistants (PDAs), MP3 players, and a dedicated catnapper device.

Users would more than likely integrate the functionality of the catnapper system into an existing electronic device they have. In this instance, the catnapper system would probably consist of an article of computer-readable media containing computer-readable instruction. When the computer executed the instruction, the computer would perform the functions and methods of the catnapper system. As mentioned, the computer may include any device that has the capabilities discussed above. This discussion will refer to this device as the catnapper system.

In FIG. 3, the catnapper system 50 is shown as a self-contained system. One skilled in the art will understand, many of the components may reside separate from each other, such as a display user interface on a computer monitor, or an audio user interface on a speaker. The system 50 includes a port 52 through which the system receives brain activity signals, also referred to as brain activity data, from an electrode, such as that mounted on the headset of FIG. 1. This port may receive the signals through a wired connection, similar to a microphone connection to the system 50, or a wireless connection, such as a radio or infrared port.

The processor 54 then analyzes the signals to determine a user somnolence level. 'Somnolence level' as used here means the user's brain activity ranging from alert to sleeping, including such stages as drowsy in between the two points, and various levels of sleep depth. The system can then store various portions of the information in the memory 62. For example, the system could store the time of day and the somnolence level, or the time of day, raw brain signals, and somnolence level, etc. The user could be presented with an interface that would allow them to enter in an activity being performed during the corresponding brain activity period, as well as many other variations.

The processor may also execute software instructions to model user behavior based upon the stored information. The modeling software 64 may reside in the processor or in a location accessible to the processor. The processor may also use the model or stored information to interact with a user's scheduling system to allow optimal scheduling in view of somnolence levels.

Once the system determines the user's somnolence level, it can provide selective feedback to the user through a user interface 56, which may have a display component 58 or an audio component 60, or both. The feedback may be selective in that the user may not want to receive feedback for certain conditions. If the brain activity shows the user to be alert, the user may not want to receive feedback. Similarly, if the brain activity indicates the user is napping and it is not time to wake the user, the feedback would not be provided. The embodiment of a process of using the catnapper system shown in FIG. 4 may assist in understanding these aspects.

Figure 4:
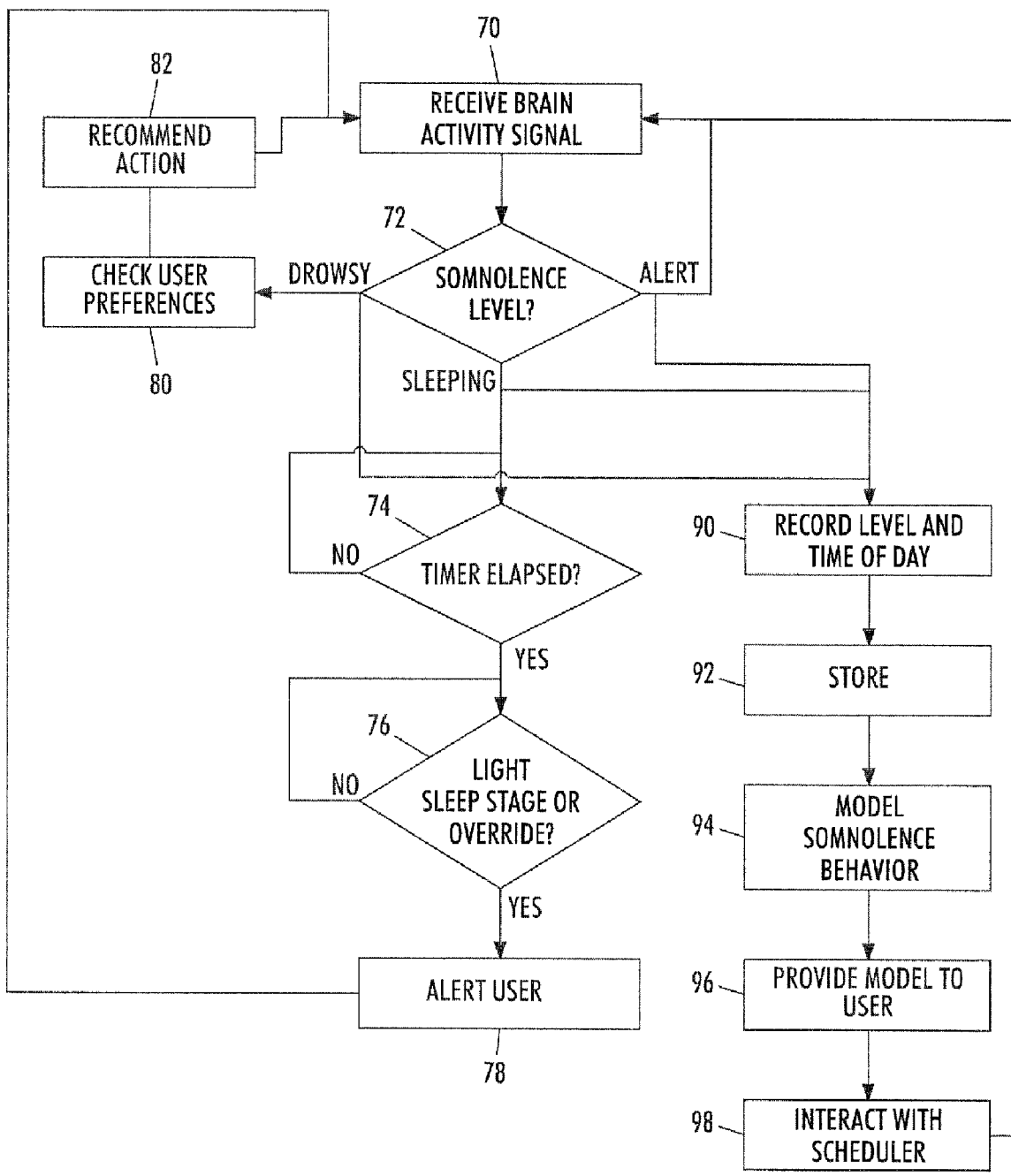
FIG. 4 shows an embodiment of a method of monitoring a user somnolence level.

FIG. 4 shows an embodiment of a method of using a catnapper system. At 70, the system receives the brain activity signal from the headset. At 72, the system determines the somnolence level. As will be discussed in more detail later, the system may make a preliminary determination, especially when the level equals 'sleep,' and then makes a more specific determination further on.

If the somnolence level is drowsy, the system may check the user preferences at 80. If the user desires, the system could recommend a nap. However, if the user indicates that the user needs to stay awake, the system could recommend a period of brief activity to 'wake' the user up. The system would recommend the action at 82. Many variations exist on this path, such as a simpler system that just determines that the user is drowsy and recommending a nap. The process of checking user preferences would become optional.

Once the system makes a recommendation at 82, it would then return to monitoring the user brain activity signals. If, for example, the user had received a recommendation to take a nap, the system would monitor when the nap began. Alternatively, if the user had performed some activity to 'wake up,' the system may register a higher level of alertness on the part of the user at 72.

Returning to alternative determinations made at 72, the system could detect that the user had a high level of alertness. In this instance, the system would just continue to monitor activity. In a simpler system, the system may not react to any brain activity that represents somnolence levels 'above' drowsy. As shown in the flow chart, however, more robust models may record data for all somnolence levels as shown at 90.

At 90, this embodiment records the somnolence level at time of day. As previously mentioned, the dimensions of the data to store at 92 may vary greatly depending upon the user preference, complexity of the system, etc. The system may utilize the stored data to model the user's somnolence behavior over the course of some period of time, such as a day or a week. The model then may be provided to the user at 96 or even to the user's scheduling program at 98. This would allow the user to optimize time for naps, periods of time for projects requiring more alert behavior, etc. The store and possible modeling process may occur from any of the somnolence levels, or from all of the levels, depending upon the user's preference.

Returning again to the somnolence level determination process at 72, the brain activity may indicate that the user is asleep. Generally, the user may set a timer for a nap time, or even a range of time, depending upon the awakening process used. If, for example, the user just wants to wake up when the time has elapsed, the user may designate a simple time, such as twenty minutes. Alternatively, the user may want to wake up only from the lighter stages of sleep, and may designate a range. For example, 'wake me up in no less than twenty minutes, but no more than thirty minutes.'

At 74, the sleep timer is checked to see if it has elapsed. The sleep time would start upon the system detecting that the user was asleep the first time. If the timer has not elapsed, the system just continues to monitor the timer. For a range of time, the system would more than likely monitor the timer for only the shortest period of time.

If the user has designated a range of times, once the shortest period of time as elapsed at 74, the system would monitor the user's sleep stage at 76. Research has shown that sleepers benefit from waking up from lighter stages of sleep, rather than deeper stages. The system would continue to monitor the user's sleep stage until either the sleep stage became light enough to allow an awakening signal to be sent, or the 'final' time period had elapsed. In the case of the final time period elapsing, the system would override the user's desire to wake up from a light stage of sleep and awaken the user anyway. The system may not include the process at 76, as it is optional. Once the time for the user's nap has elapsed, however that time is determined, the system would alert the user at 78, such as with a blinking display, audible alarm, various music, natural sounds, or audio learning materials, etc.

It should also be noted that the method could be arranged such that the determination of sleep level occurs at 72, as mentioned previously. The determination at 72 would then have at least one other branch based upon level/stage of sleep, rather than just an initial determination of 'sleep,' and the process 76 would become part of that branch. Various other modifications to the process exist and would be considered within the scope of this disclosure.

In this manner, the user can utilize a catnapper system to optimize napping behavior. The ability to take naps has proven to increase a user's effectiveness. This system provides options for managing and controlling napping behavior.

It will be appreciated that several of the above-disclosed and other features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the following claims.

What is claimed is:

1. A system, comprising:
    a port to receive brain activity data of a user;
    a processor to detect a beginning time of a user nap based upon the brain activity data and to store the beginning time and time of day; and
    a user interface to notify the user when a predetermined nap time has elapsed.

2. The system of claim 1, the system further comprising a store.

3. The system of claim 1, the processor further to generate a model of brain activity over a defined period of time.

4. The system of claim 3, the user interface further to present the model of brain activity to the user.

5. The system of claim 3, the processor to make recommendations to the user through the user interface based upon the model.

6. The system of claim 1, the user interface to allow the user to select the predetermined nap time.

7. The system of claim 1, the processor further to detect a user drowsiness level and to make a recommendation to the user.

8. The system of claim 7, the recommendation further comprising one of either to take a nap or to perform an alerting activity to stay awake.

9. A method of monitoring a user somnolence level, comprising:
    receiving brain activity data from a user;
    determining a somnolence level from the brain activity data;
    storing data including the somnolence level and time of day;
    if the somnolence level is sleep, determining using a processor if a nap has progressed to a waking point; and
    if the nap has progressed to a waking point, alerting the user.

10. The method of claim 9, further comprising if the somnolence level is drowsy, providing a recommendation to the user to take a nap.

11. The method of claim 9, further comprising using the data to generate a model of user somnolence behavior.

12. The method of claim 11, further comprising providing the model to a user calendar to allow a user to plan activities using the model.

13. The method of claim 9, receiving brain activity data from a user further comprising receiving the data as signals from a wireless electroencephalogram headset.

14. The method of claim 9, wherein alerting the user comprises alerting the user when the user is in a light sleep stage.

15. An article of computer-readable media storing instructions that, when executed, cause the computer to:
    receive brain activity data from a user;
    determine a somnolence level from the brain activity data;
    storing the somnolence level and time of day;
    if the somnolence level is sleep, determine if a nap timer has elapsed; and
    if the nap timer has elapsed, alert the user.

16. The article of claim 15, the instructions further causing the computer to make a recommendation to the user to take a nap, if the somnolence level is drowsy.

17. The article of claim 15, the instructions further causing the computer to present a user interface to allow the user to set the nap timer.

* * * * *